(12) United States Patent
Morales

(10) Patent No.: US 6,277,110 B1
(45) Date of Patent: Aug. 21, 2001

(54) METHOD OF CRIMPING AN INTRAVASCULAR STENT ONTO A BALLOON CATHETER

(75) Inventor: Stephen A. Morales, Mountain View, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/419,655

(22) Filed: Oct. 18, 1999

Related U.S. Application Data

(62) Division of application No. 09/030,261, filed on Feb. 25, 1998, now Pat. No. 6,024,737.

(51) Int. Cl.$^7$ .................................................. A61B 17/00
(52) U.S. Cl. ........................................................... 606/1
(58) Field of Search ............................... 606/1, 108, 198; 623/1.11; 81/345; 29/282, 516

(56) References Cited

U.S. PATENT DOCUMENTS

| | | |
|---|---|---|
| 696,289 | 3/1902 | Williams . |
| 2,553,479 | 5/1951 | Schmarje et al. . |
| 4,468,224 | 8/1984 | Enzmann et al. . |
| 4,576,142 | 3/1986 | Schiff . |
| 4,644,936 | 2/1987 | Schiff . |
| 4,681,092 | 7/1987 | Cho et al. . |
| 4,697,573 | 10/1987 | Schiff . |
| 4,901,707 | 2/1990 | Schiff . |
| 4,907,336 | 3/1990 | Gianturco . |
| 5,132,006 | 7/1992 | Charlesworth et al. . |
| 5,133,732 | 7/1992 | Wiktor . |
| 5,183,085 | 2/1993 | Timmermans . |
| 5,189,786 | 3/1993 | Ishikawa et al. . |
| 5,209,799 | 5/1993 | Vigil . |
| 5,336,234 | 8/1994 | Vigil et al. . |
| 5,437,083 | 8/1995 | Williams et al. . |
| 5,546,646 | 8/1996 | Williams et al. . |
| 5,609,606 | 3/1997 | O'Boyle . |
| 5,611,807 | 3/1997 | O'Boyle . |
| 5,626,604 | 5/1997 | Cottone, Jr. . |
| 5,630,830 | 5/1997 | Verbeek . |
| 5,653,691 | 8/1997 | Rupp et al. . |
| 5,672,169 | 9/1997 | Verbeek . |
| 5,725,519 | 3/1998 | Penner et al. . |
| 5,738,674 | 4/1998 | Williams et al. . |
| 5,746,764 | 5/1998 | Green et al. . |
| 5,783,227 | 7/1998 | Dunham . |

(List continued on next page.)

FOREIGN PATENT DOCUMENTS

| | | |
|---|---|---|
| 2211694 | 2/1998 | (CA) . |
| 0 562 478 A1 | 9/1993 | (EP) . |
| 0 873 731 A1 | 10/1998 | (EP) . |
| 159065 | 2/1921 | (GB) . |
| 02180275A | 7/1990 | (JP) . |
| 4-45187 | 7/1992 | (JP) . |
| 7-47135 | 2/1995 | (JP) . |
| 7-67967 | 3/1995 | (JP) . |
| WO 98/14120 | 4/1998 | (WO) . |
| WO 98/19633 | 5/1998 | (WO) . |

OTHER PUBLICATIONS

U.S. Application No. 08/795,335, filed Feb. 4, 1997.
U.S. Application No. 08/837,771, filed Apr. 22, 1997.
U.S. Application No. 08/962,632, filed Nov. 3, 1997.
The *eXTraordinary Stent*, C.R. Bard Brochure (undated).

Primary Examiner—Jeffrey A. Smith
(74) Attorney, Agent, or Firm—Fulwider Patton Lee & Utecht, LLP

(57) ABSTRACT

A slidably-engageable device for enabling effective crimping of an intravascular stent onto a balloon catheter assembly. The stent crimping device includes at least one compressible and releasable loop portion which enables the stent and catheter assembly to be supported thereon, and is compressible radially inwardly to effectively crimp the stent onto the balloon catheter assembly.

8 Claims, 5 Drawing Sheets

U.S. PATENT DOCUMENTS

| | | |
|---|---|---|
| 5,785,715 | 7/1998 | Schatz . |
| 5,810,838 | 9/1998 | Solar . |
| 5,810,873 | 9/1998 | Morales . |
| 5,836,952 | 11/1998 | Davis et al. . |
| 5,860,966 | 1/1999 | Tower . |
| 5,893,867 | 4/1999 | Bagaoisan et al. . |
| 5,911,452 | 6/1999 | Yan . |
| 5,920,975 * | 7/1999 | Morales ................................. 29/282 |
| 5,927,016 * | 10/1999 | Morales ............................... 606/198 |
| 6,024,737 * | 2/2000 | Morales .................................... 606/1 |
| 6,063,102 * | 5/2000 | Morales ............................... 606/198 |
| 6,141,855 * | 11/2000 | Morales ................................. 29/516 |

* cited by examiner

METHOD OF CRIMPING AN INTRAVASCULAR STENT ONTO A BALLOON CATHETER

This is a divisional application of application Ser. No. 09/030,261, filed Feb. 25, 1998, now U.S. Pat. No. 6,024,737, the contents of which are hereby incorporated by reference.

BACKGROUND OF THE INVENTION

1. Field of the Invention

This invention relates to a stent crimping device of the type that will enable the user to crimp a stent onto the distal end of a balloon catheter assembly, for example of the kind used in a typical percutaneous transluminal coronary angioplasty (PTCA) procedure.

2. Description of the Related Art

In a typical PTCA procedure, for compressing lesion plaque against the artery wall to dilate the artery lumen, a guiding catheter is percutaneously introduced into the cardiovascular system of a patient through the brachial or femoral arteries and advanced through the vasculature until the distal end is in the ostium. A guidewire and a dilatation catheter having a balloon on the distal end are introduced through the guiding catheter with the guidewire sliding within the dilatation catheter. The guidewire is first advanced out of the guiding catheter into the patient's coronary vasculature, and the dilatation catheter is advanced over the previously advanced guidewire until the dilatation balloon is properly positioned across the lesion. Once in position across the lesion, a flexible, expandable, preformed balloon is inflated to a predetermined size at relatively high pressures to radially compress the atherosclerotic plaque of the lesion against the inside of the artery wall and thereby dilate the lumen of the artery. The balloon is then deflated to a small profile, so that the dilatation catheter can be withdrawn from the patient's vasculature and blood flow resumed through the dilated artery. While this procedure is typical, it is not the only method used in angioplasty. Other methods to open a vessel are known, such as atherectomies and plaque dissolving drugs.

In angioplasty procedures of the kind referenced above, a restenosis of the artery may develop over several months, which may require another angioplasty procedure, a surgical bypass operation, or some method of repairing or strengthening the area. To reduce the chance of the development of restenosis and strengthen the area, a physician can implant an intravascular prosthesis for maintaining vascular patency, typically called a stent. A stent is a device used to hold tissue in place in a vessel or to provide a support for a vessel to hold it open so that blood flows freely. A variety of devices are known in the art for use as stents, including expandable tubular members, in a variety of patterns, that are able to be crimped onto a balloon catheter, and expanded after being positioned intraluminally on the balloon catheter, and that retain their expanded form. Typically, the stent is loaded and crimped onto the balloon portion of the catheter, and advanced to a location inside the artery at the lesion. The stent is then expanded to a larger diameter, by the balloon portion of the catheter, to implant the stent in the artery at the lesion. Examples of stents and delivery catheters as described are disclosed in more detail in U.S. Pat. No. 5,102,417 (Palmaz), U.S. Pat. No. 5,569,295 (Lam), and U.S. Pat. No. 5,514,154 (Lau et al.).

However, if the stent is not effectively crimped onto the catheter balloon portion, when the catheter is advanced in the patient's vasculature the stent may move or even slide off the catheter balloon portion in the body lumen or coronary artery prior to expansion, and may block the flow of blood, requiring procedures to remove the stent.

In procedures where the stent is placed over the balloon portion of the catheter, the stent must be crimped onto the balloon portion to prevent the stent from sliding off the catheter when the catheter is advanced in the patient's vasculature. In the past this crimping was often done by hand, which does not provide optimum results due to the uneven force being applied, resulting in non-uniform crimps. In addition, it was difficult to judge when a uniform and reliable crimp had been applied. The prior art tools and methods have not been entirely adequate in achieving a uniform crimp. Stent designs generally are based on a uniform metal-to-artery ratio for the highest success rate, thus a non-uniformly crimped stent may result in an unevenly expanded stent in the vessel or artery, which is undesirable.

SUMMARY OF THE INVENTION

This invention is directed to a vascular prosthesis crimping device which enables uniform and tight crimping of a stent onto a catheter balloon portion, to better secure the stent onto the catheter for delivery of the stent through the patient's vasculature. The present invention attempts to solve several problems associated with crimping stents onto balloon catheters.

In an exemplary embodiment of the present invention, the stent crimping device includes a compressible and releasable loop portion of a flexible sleeve in a hand tool, secured at its opposed ends to slidably-engageable members of the hand tool. The loop portion is compressible radially inwardly by the application of slidably-engageable compressive force to the hand tool by the user, to uniformly and tightly crimp the stent onto the balloon catheter assembly. The loop portion is further releasable upon release by the user of the compressive force applied to the hand tool, to enable release of the stent crimped onto the balloon catheter assembly.

The crimping device enables the stent to be uniformly and tightly crimped onto the distal end of a balloon catheter, reducing the risk that the stent may slide off the catheter balloon portion. It is further easy to use in performing the stent crimping procedure.

In an exemplary method of crimping the stent onto the balloon portion of a catheter, the crimping device is designed to be hand-held and the crimping method performed by one person. The stent is first pre-loaded onto the balloon by sliding the stent over the deflated balloon. The stent and balloon catheter assembly are placed or positioned within the radially compressible device and supported therein so that the stent and balloon are positioned within the loop portion of the flexible sleeve. While the user holds the stent and balloon catheter assembly in one hand, a compressive force is applied using the other hand by applying slidingly engageable force with the crimping device. As the loop portion constricts in diameter, it will uniformly and tightly compress the stent onto the balloon portion of the catheter. Thereafter, the user releases the compressive force thereby releasing tension on the loop so that the stent, now tightly compressed onto the balloon portion of the catheter, can be removed from the crimping device.

These and other advantages of the invention will become more apparent from the following detailed description thereof when taken in conjunction with the accompanying drawings.

DETAILED DESCRIPTION OF THE PREFERRED EMBODIMENTS

Figure 1:
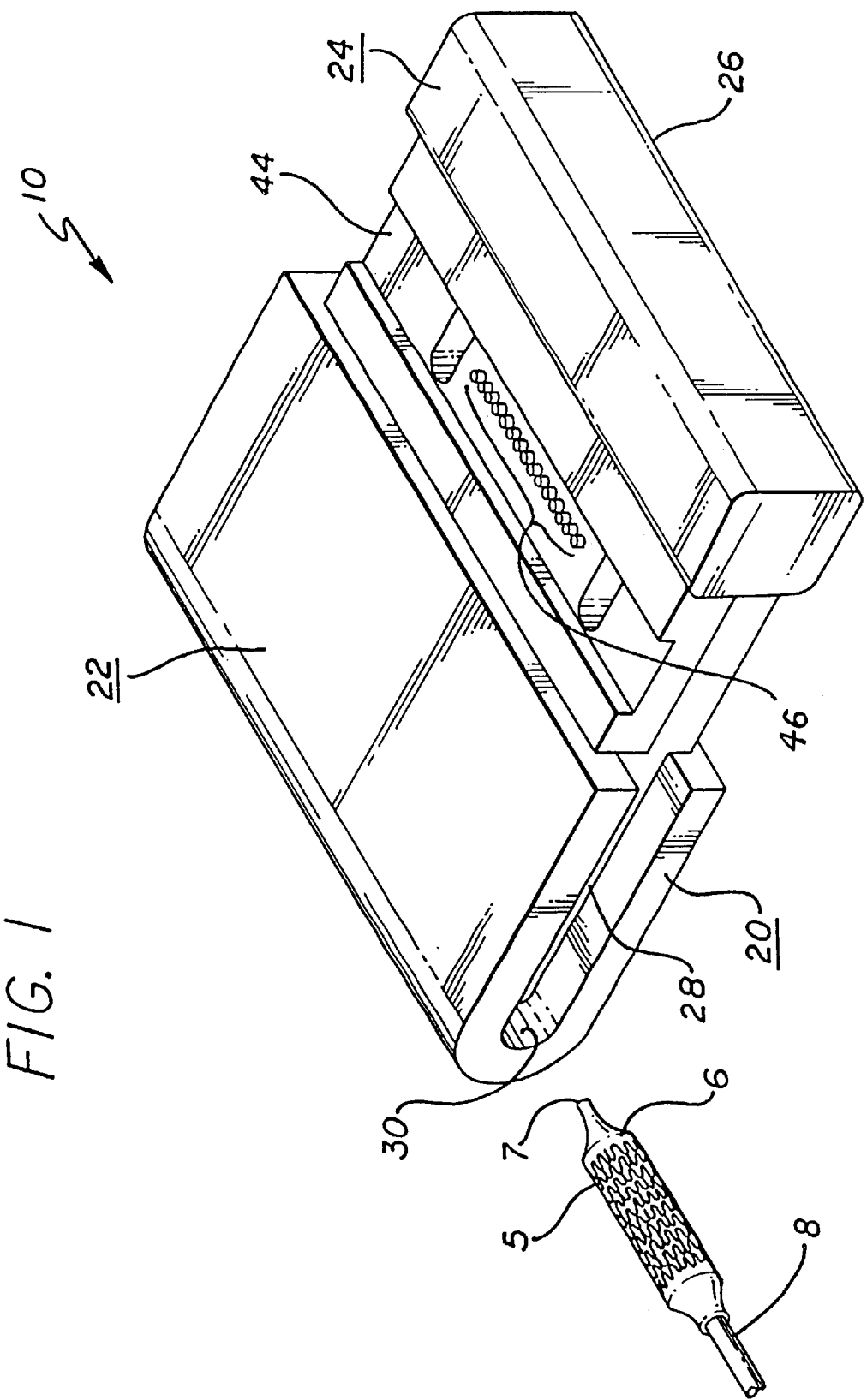
FIG. 1 is a perspective view of an exemplary embodiment of the present invention, in which the slidably-engaging member is slidably moved into engagement with the receiving member.
Figure 2:
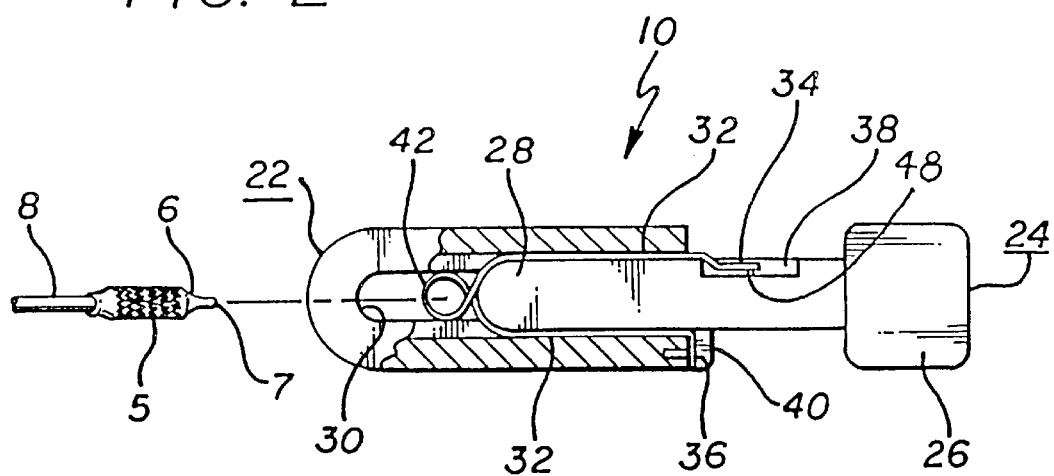
FIG. 2 is a side elevational view of the exemplary embodiment of the present invention in the expanded loop portion condition.
Figure 3:
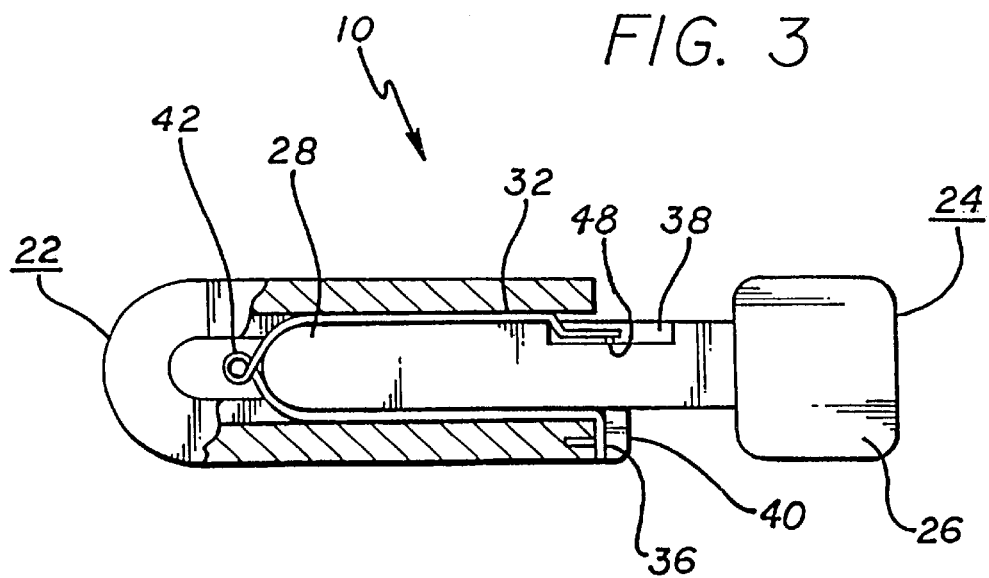
FIG. 3 is a side elevational view of the exemplary embodiment of the present invention in which the loop portion of the hand tool is in compressed condition for crimping the stent onto the catheter balloon portion.
Figure 4:
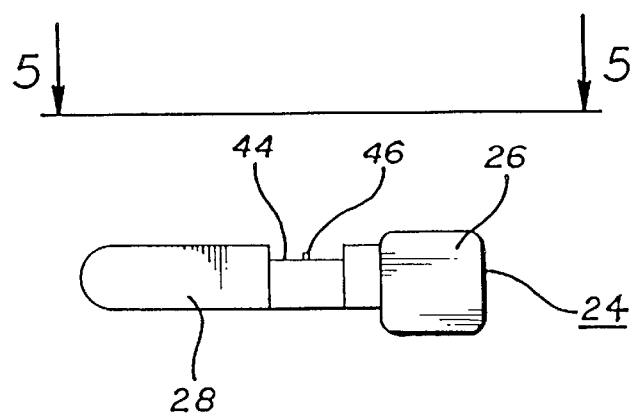
FIG. 4 is a side elevational view of the slidably engaging member and first securing member.
Figure 5:
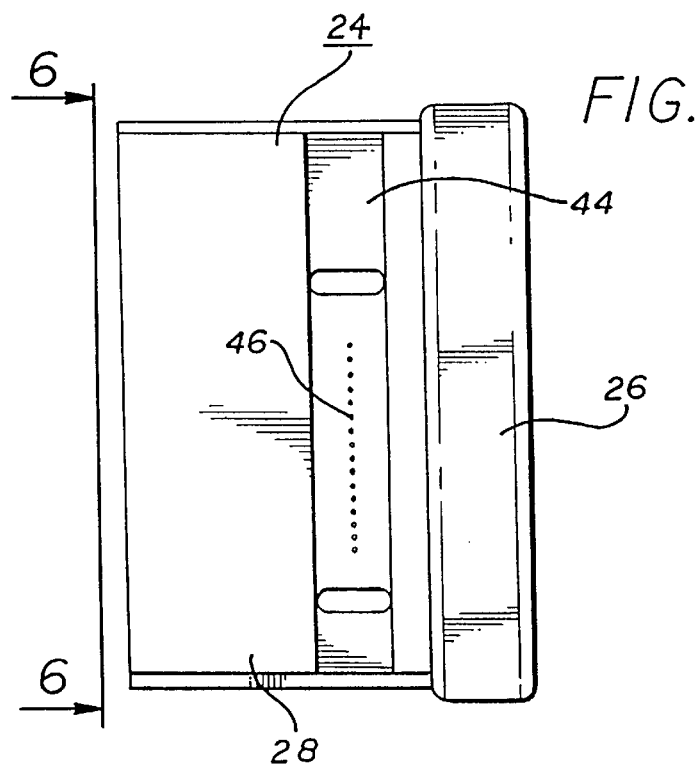
FIG. 5 is a top plan view of the slidably engaging member and first securing member, taken along line 5—5 of FIG. 4.
Figure 6:
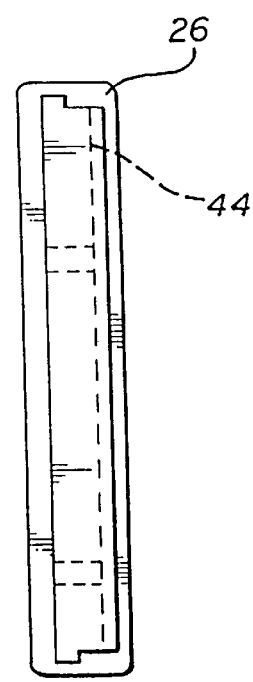
FIG. 6 is an end view of the first securing member taken along line 6—6 of FIG. 5.
Figure 7:
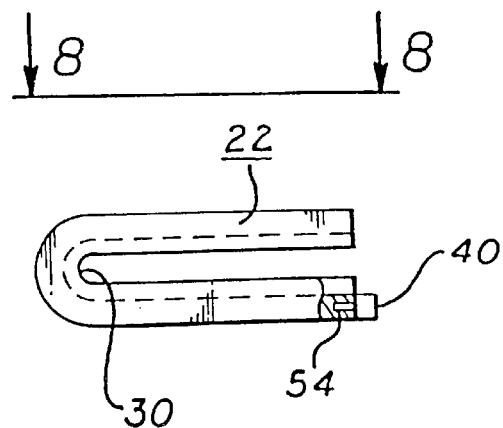
FIG. 7 is a side elevational view of the receiving member and second securing member.
Figure 8:
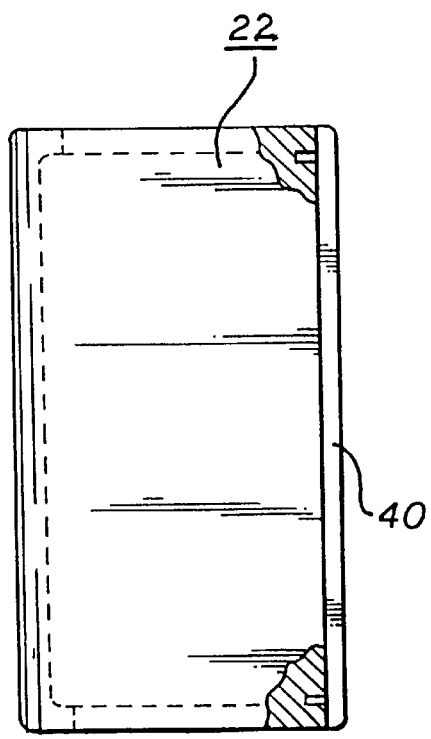
FIG. 8 is a top plan view of the receiving member and second securing member, taken along line 8—8 of FIG. 7.
Figure 9:
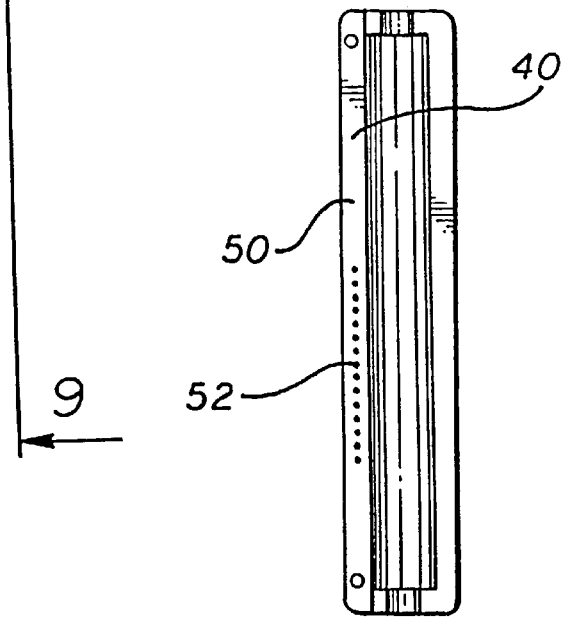
FIG. 9 is an end view of the second securing member taken along line 9—9 of FIG. 8.

Device 10 comprises a tool 20 for enabling effective crimping of an intravascular stent 5 onto the collapsed balloon portion 6 adjacent the distal end 7 of a balloon catheter assembly 8. In the exemplary embodiment of device 10, as shown in FIGS. 1–9, tool is adapted to be held in the hand of the user, so as to enable stent 5 and catheter 8 to be supported in tool 20, and to enable the user to apply compressive force to tool 20 to crimp the stent on the catheter.

Tool 20 includes receiving member 22, and slidably engaging member 24 that is slidably movable into engagement with receiving member 22. Slidably engaging member 24 includes a handle portion 26, and a projecting portion 28 slidably engageable with the receiving member. Receiving member 22 has a groove 30 therein. Projecting portion 28 of slidably-engaging member 24 and groove 30 of receiving member 22 are engageable and generally complementary in shape. Receiving member 22 and slidably engaging member 24 are both preferably translucent.

Tool 20 further includes a crimping member 32, secured at its ends to slidably-engaging member 24 and receiving member 22, for supporting stent 5 and catheter 8 therein. Member 32 includes a first end 34, adapted to be secured to slidably-engageable member 24, and a second end 36, at the end of member 32 opposite the first end, adapted to be secured to receiving member 22. A first sewing member 38 is adapted to secure first end 34 to slidably-engaging member 24, and a second securing member 40 is adapted to secure second end 36 to receiving member 22. Member 32 further includes at least one compressible loop portion 42 wherein the portion of balloon catheter assembly 8 with stent 5 loaded thereon may be supported. Supporting member 32 is comprised of compressible material, such that upon sliding slidably-engaging member 24 into engagement with receiving member 22, loop portion 42 is compressed radially inwardly to crimp stent 5 balloon portion 6. In other words, the diameter of loop portion 42 decreases as members 22,24 are squeezed together, thereby crimping stent 5 onto balloon portion 6. Upon release of force applied by slidably engaging member 24, by pulling slidably engaging member 24 out of engagement with receiving member 22, the crimped stent 5 and the catheter may be removed from loop portion 42. The compressible material of which member 32 is comprised is preferably a polyester film, such as Mylar®, which is a registered trademark of Du Pont Corporation, Wihnington, Del. Repeated squeezing of members 22,24 together to compress loop portion 42 on the stent will result in an increasingly tighter crimped stent on the balloon.

In the embodiment shown in FIGS. 1–9, slidably-engageable member 24 includes a recessed portion 44 including a plurality of pegs 46 projecting therefrom, and first securing member 38 includes a slot 48 for engaging crimping member 32 and first member pegs 46, to align and secure crimping member 32 to slidably-engaging member 24. Second securing member 40 includes a facing surface 50 including a plurality of pegs 52 projecting therefrom, and receiving member 22 includes a slot 54 for engaging crimping member 32 and second securing member pegs 52, to align and secure crimping member 32 to receiving member 22.

Figure 10:
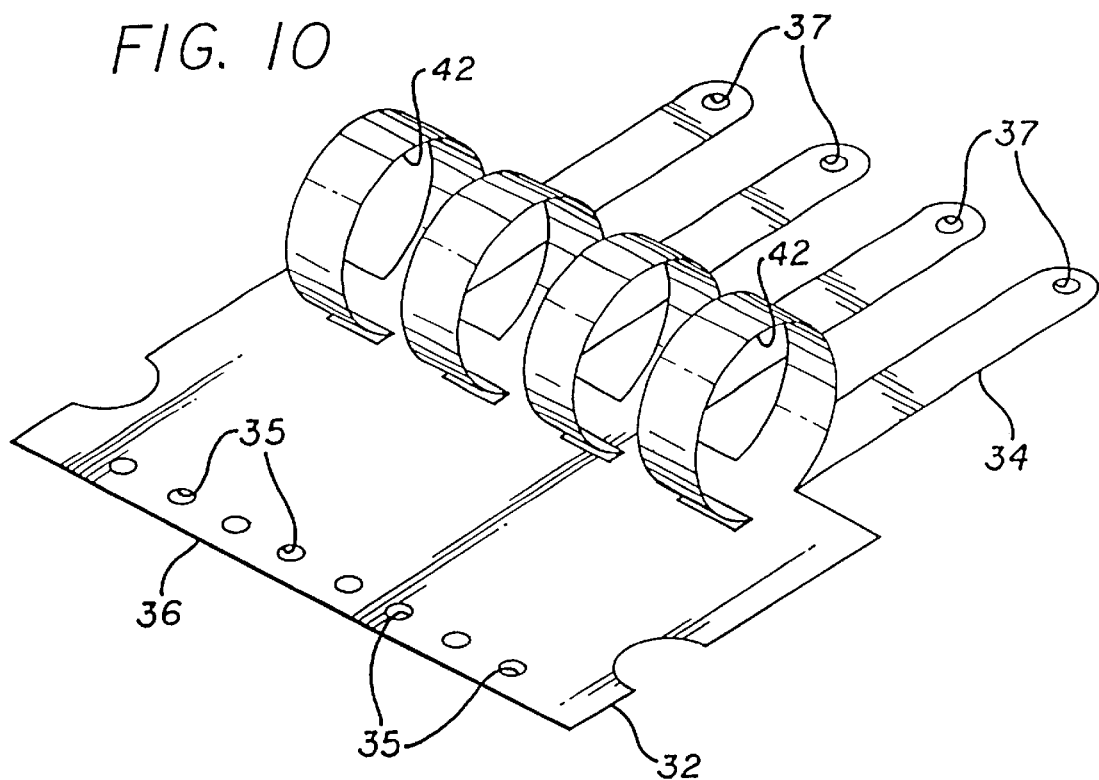
FIG. 10 is a perspective view depicting one embodiment of the loop portion.
Figure 11:
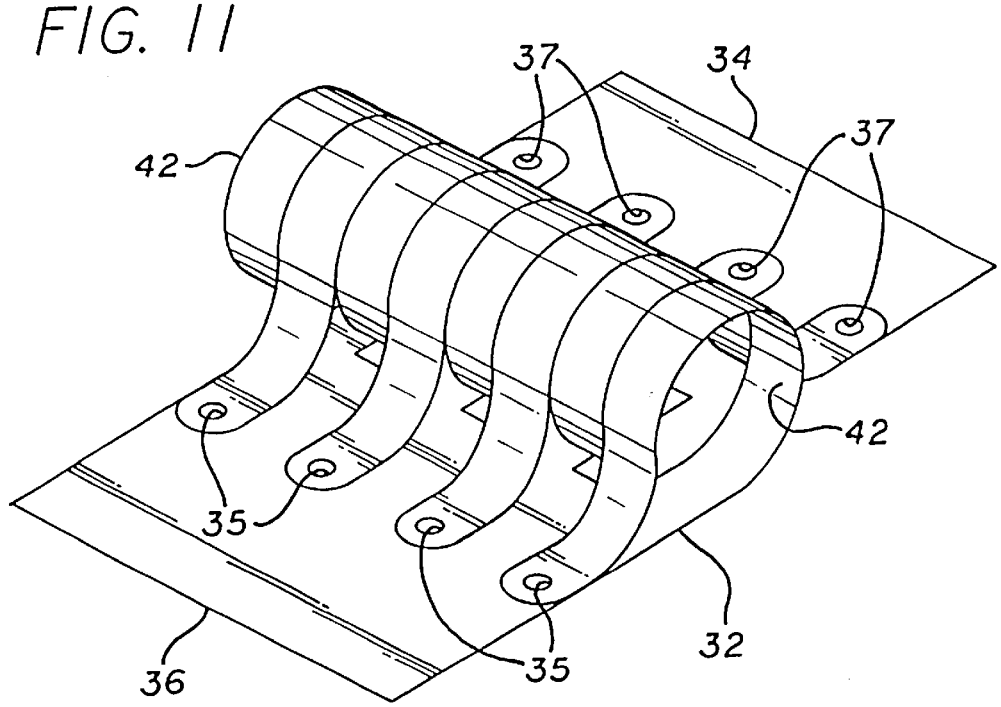
FIG. 11 is a perspective view depicting an alternative embodiment of the loop portion.

As seen in FIGS. 10 and 11, two preferred alternative embodiments of member 32 are depicted. Loop portion 42 includes a plurality of loops and it is sized to accept stent 5 and balloon portion 6 of the catheter prior to crimping. As the slidably-engaging member 24 and receiving member 22 are pushed together, first end 34 and second end 36 move in opposite directions, thereby constricting loop portion 42 onto the stent and crimping it onto the balloon with increasing force. As shown in FIGS. 10 and 11, in order to secure member 32 and assist in placing ends 34, 36 in tension, holes 35 align with pegs 52 while holes 37 align with pegs 46. Thus, ends are securely attached to the respective sets of pegs so that as members 22, 24 are squeezed together, ends 35, 37 move with pegs 46, 52.

In operation, to load stent 5 onto collapsed balloon portion 6 of balloon catheter assembly 8, stent 5 is mounted over the balloon so that the stent overlies the balloon portion but is not crimped thereon. To enable stent 5 to be crimped onto catheter balloon portion 6, the stent and the catheter balloon portion may be inserted into and supported in loop portion 42 of tool supporting member 32. At this point, stent 5 is not crimped onto the balloon because it has not been compressed.

To crimp stent 5 onto catheter balloon portion 6, the user of tool 20 secures the ends 35,37 of member 32 to slidably-engaging member 24 and receiving member 22. Member 32 is secured to slidably-engaging member 24 by positioning first end 34 of member 32 between pegs 46 in recessed portion 44 of slidably-engaging member 24 and pressing slot 48 in first securing member 38 into engagement with member 32 and pegs 46 in slidably-engaging member 24. Member 32 is secured to receiving member 22 by positioning second end 36 of member 32 between pegs 52 in facing surface 50 of second securing member 40 and pressing pegs 52 in second securing member 40 into engagement with member 32 and slot 54 in receiving member 22.

The user of tool 20 may then apply force to slide slidably-engageable member 24 into engagement with receiving member 22, such that as projecting portion 28 of slidably-engageable member 24 pushes crimping member 32, secured at both ends 35,37, into groove 30 of receiving member 22. This motion will then move first end 35 and second end 37 in opposite directions which causes the diameter of loop portion 42 to become smaller and compress radially inwardly, thereby compressing stent 5 radially inwardly onto catheter balloon portion 6.

After stent 5 has been crimped onto catheter balloon portion 6, the user may release the force applied to crimping member 32 by pulling slidably-engaging member 24 out of engagement with receiving member 22. This motion allows loop portion 42 to increase in diameter. The user may then release member 32 from being secured by first member 38 and second member 40, by disengaging first member 38 from member 32 and slidably-engageable member 24, and disengaging second member 40 from member 32 and receiving member 22, enabling removal of crimped stent and catheter balloon portion from loop portion 42. Balloon catheter assembly 8, with stent 5 crimped thereon, is then ready for insertion into the body of the patient for deployment of the stent therein.

A novel feature of the present invention is the crimping tool's ability to vary the constriction of various parts of the stent. Thus, the stent will be crimped harder in some places, localizing the traction (interface) between the stent and the balloon. Even though there are variations in crimping force on the stent, it remains within the bounds of uniformity. In the case of a coronary artery stent, the crimped stent may have diameters along its length in the range of 0.003 to 0.005 inch and still be considered a uniform crimp with good traction or holding force on the balloon.

While in the preferred embodiment the stent described is intended to be an intraluminal vascularprosthesis for use within a blood vessel, and the balloon delivery catheter is of the same or similar to that used in therapeutic coronary angioplasty, it will be appreciated by those skilled in the art that modifications may be made to the present invention to allow the present invention to be used to crimp any type of prosthesis. The present invention is not limited to stents that are deployed in a patient's vasculature, but has wide applications to crimping any type of graft, prosthesis, liner or similar structure. Furthermore, the stent may be delivered not only into coronary arteries, but into any body lumen. Other modifications can be made to the present invention by those skilled in the art without departing from the scope thereof.

What is claimed is:

1. A method of crimping an intravascular stent onto a balloon catheter assembly, comprising:

placing a portion of the balloon catheter assembly, on which the stent is positioned, in a radially compressible device;

applying slidably-engageable compressive force to compress the compressible device radially inwardly, including applying force to a slidably engageable member and a receiving member to which the stent and catheter supporting means are secured, and compressing the slidably-engageable member and the receiving member so as to compress the supporting means to crimp the stent onto the catheter portion; and releasing the compressive force, to enable removal of the crimped stent and catheter portion.

2. A method as in claim 1, wherein the step of placing the stent and catheter portion in a compressible device comprises placing the catheter portion in a compressible portion of means for supporting the stent and catheter portion, in a device adapted to be held in the hand of the user, so as to enable the user to apply compressive force thereto.

3. A method as in claim 2, wherein the step of supporting the stent and catheter portion in the compressible device comprises supporting the stent and catheter portion in at least one loop in a sleeve, and the step of applying force to the compressible device comprises applying force to the at least one loop in the sleeve.

4. A method for crimping a stent onto a balloon portion of a catheter, comprising the steps of:

providing a crimping member having a flexible sleeve, the flexible sleeve having a loop portion capable of changing from at least a first larger diameter to a second smaller diameter, and the flexible sleeve having a first end and a second end;

providing a projecting member;

providing a receiving member, wherein the projecting member and receiving member have generally complementary shapes;

attaching the first end of the flexible sleeve to the receiving member and the second end to the projecting member;

slidably engaging the receiving member with the projecting member;

positioning the stent and balloon within the loop portion;

translating the receiving member relative to the projecting member to pull on the ends of the flexible sleeve to constrict the loop portion from the first larger diameter to the second smaller diameter, thereby applying compressive forces to crimp the stent onto the balloon portion of the catheter.

5. The method of claim 4, wherein the step of providing a receiving member includes providing a groove in the receiving member configured for receiving the complementary-shaped projecting member.

6. The method of claim 4, wherein the step of providing a crimping member having a flexible sleeve includes providing a flexible polymeric material.

7. The method of claim 4, wherein the step of providing a crimping member includes providing a flexible sleeve including first and second ends and an opening therein, and passing the first end through the opening to form a loop.

8. The method of claim 4, wherein the step of translating the receiving member relative to the projecting member includes pushing the receiving member and the projecting member together.

* * * * *